United States Patent
Badhwar (10) Patent No.: US 9,358,109 B2
(45) Date of Patent: Jun. 7, 2016

(54) TRANSCORPOREAL DELIVERY SYSTEM AND METHOD

(76) Inventor: Vinay Badhwar, Celebration, FL (US)

( * ) Notice: Subject to any disclaimer, the term of this patent is extended or adjusted under 35 U.S.C. 154(b) by 694 days.

(21) Appl. No.: 12/930,526

(22) Filed: Jan. 10, 2011

(65) Prior Publication Data

US 2011/0172764 A1 Jul. 14, 2011

Related U.S. Application Data

(60) Provisional application No. 61/335,843, filed on Jan. 13, 2010.

(51) Int. Cl.
*A61F 2/24* (2006.01)

(52) U.S. Cl.
CPC .............. *A61F 2/2427* (2013.01); *A61F 2/2403* (2013.01); *A61F 2/243* (2013.01); *A61F 2/2412* (2013.01); *A61F 2/2439* (2013.01)

(58) Field of Classification Search
CPC ... A61F 2/2403; A61F 2/2427; A61F 2/2412; A61F 2/243; A61F 2/2439
USPC ................ 623/2.1, 2.11–2.19, 2.38, 2.4, 2.41
See application file for complete search history.

(56) References Cited

U.S. PATENT DOCUMENTS

| | | | | |
|---|---|---|---|---|
| 5,156,621 A * | 10/1992 | Navia et al. | ................... | 623/2.12 |
| 5,549,665 A * | 8/1996 | Vesely et al. | ................. | 623/2.14 |
| 6,296,662 B1 * | 10/2001 | Caffey | .......................... | 623/2.18 |
| 6,312,464 B1 * | 11/2001 | Navia | ............................ | 623/2.12 |
| 6,338,740 B1 * | 1/2002 | Carpentier | ................... | 623/2.13 |
| 6,454,799 B1 * | 9/2002 | Schreck | ........................ | 623/2.18 |
| 6,569,196 B1 * | 5/2003 | Vesely | .......................... | 623/2.14 |
| 7,044,966 B2 * | 5/2006 | Svanidze et al. | .............. | 623/2.1 |
| 7,311,730 B2 * | 12/2007 | Gabbay | ......................... | 623/2.38 |
| 7,399,315 B2 * | 7/2008 | Iobbi | ............................. | 623/1.26 |
| 7,534,261 B2 * | 5/2009 | Friedman | ..................... | 623/2.17 |
| 7,717,955 B2 * | 5/2010 | Lane et al. | .................... | 623/2.41 |
| 2005/0096739 A1 * | 5/2005 | Cao | ............................... | 623/2.19 |
| 2006/0135964 A1 * | 6/2006 | Vesely | .......................... | 606/108 |
| 2006/0247570 A1 * | 11/2006 | Pokorney | .......................... | 604/9 |
| 2007/0016289 A1 * | 1/2007 | Johnson | ........................ | 623/2.17 |
| 2007/0129795 A1 * | 6/2007 | Hill et al. | ...................... | 623/2.11 |
| 2007/0219629 A1 * | 9/2007 | Bokros et al. | ................. | 623/2.11 |
| 2008/0071367 A1 * | 3/2008 | Bergin et al. | ................. | 623/2.11 |
| 2008/0177381 A1 * | 7/2008 | Navia et al. | .................. | 623/2.11 |

OTHER PUBLICATIONS

Canadian Office Action dated Aug. 13, 2015, in Canadian Patent Application 2,787,046.

* cited by examiner

*Primary Examiner* — Jing Ou
(74) *Attorney, Agent, or Firm* — Ramey & Schwaller, LLP (57) ABSTRACT

A transcorporeal delivery system and method provide the ability to perform minimally invasive valve replacement surgery. The transcorporeal delivery system provides a device and method for transcorporeal (traversing the body surface) low profile delivery of a replacement valve, intracorporeal (inside the body) stabilization for suture placement, and minimal change to current valve replacement surgical implantation techniques.

3 Claims, 9 Drawing Sheets

TRANSCORPOREAL DELIVERY SYSTEM AND METHOD

This application claims priority from U.S. Provisional Patent Application having Ser. No. 61/335,843, filed Jan. 13, 2010.

The invention disclosed and claimed herein deals with a transcorporeal delivery system and method for valve replacement surgery that is minimally invasive.

BACKGROUND OF THE INVENTION

It is contemplated by the inventor herein that all valves of the human body can be replaced by the inventive devices set forth herein eventhough heart valves are set forth primarily to describe the inventive device use.

Heart valve replacement surgery conventionally involves a full median sternotomy incision. Due to the invasiveness of this approach, medical referral culture for valve surgery has historically followed a policy of delay and observation until patient symptoms are advanced; despite well accepted guidelines that outline the benefit of earlier treatment of valvular heart disease. Recently, less invasive or "minimally invasive" approaches to valve surgery can be performed with equal or superior long term results. This represents one of the most significant recent market advances of valvular therapy. Patients and their physicians that are exposed to the renewed understanding of the concerns of delaying valve surgery now have a newer option that is swinging the referral patterns to earlier surgery and thus increasing volumes in many centers that focus on minimally invasive valve surgery.

Minimally invasive approaches to surgical valve replacement therapy have been performed via mini sternotomy yet a growing majority are currently being performed with access between the rib cage via a mini-right thoracotomy. These procedures are often aided by femoral or endo-direct cannulation and port access techniques. As instrumentation improves, the principle working incision has the ability to further reduce in size in a step-wise manner towards the near future goal of total endoscopic therapy. Industry improvements in cannulation and instrumentation are proceeding at an exponential rate while market-ready valve repair and replacement design has lagged significantly behind. Currently, the principle factor for dictating incision size in current minimally invasive valve techniques is the size and immobility of available valve prostheses.

Current stented biologic tissue valve design principles include fixed bovine or porcine tissue affixed to a flexible textile material sleeve which is in turn attached to a rigid stent composite of moldable plastic which in some cases may include wire reinforcement, and a fixed malleable, plastic, flexible textile material sewing ring.

The design of an ideal tissue valve for minimally invasive surgical implantation should include improvements of the current commonly used stented tissue valves to address the following: Transcorporeal (traversing the body surface) low profile delivery, intracorporeal (inside the body) stabilization for suture placement, and minimal change to current valve replacement surgical implantation techniques in order to enhance surgical adoption while maintaining procedural effectiveness and safety.

The following for the modification of, but not limited to, biologic tissue prostheses addresses each of these areas while minimally altering current tissue valve production and preservation methods.

The human heart has four valves that control the direction of blood flow through the four chambers of the heart. On the left or systemic side of the heart are the mitral valve, located between the left atrium and the left ventricle, and the aortic valve located between the left ventricle and the aorta. On the right or pulmonary side of the heart are the tricuspid valves, located between the right atrium and the right ventricle, and the pulmonary valve, located between the right ventricle and the pulmonary artery.

For purposes of this invention, therapeutic utility is feasible with all valve positions and pathologies requiring replacement included herein eventhough this disclosure and discussion will primarily reference aortic and mitral replacement.

THE INVENTION

Thus, what is disclosed and claimed herein is a transcorporeal delivery system comprising a heart valve; a valve fixation device surmounting said heart valve; a valve fixation device delivery arm 32 (FIG. 3), and a mechanism for deploying said valve system and valve fixation device.

The valve comprises at least two moveable leaflets attached to a fabric Constructed sewing ring. The sewing ring is configured in the shape of the heart valve base, wherein the sewing ring is surmounted by a malleable memory alloy support. Nitinol™ is an example of such a malleable memory alloy support and is used herein for the purpose of discussion Malleable metal alloy support is in wire form and has a configuration at its base essentially matching the configuration of the heart valve base. The malleable metal alloy support has three vertically extended portions that are equally spaced from each other around the base.

The malleable metal alloy support has three bands around the base spaced equally between the vertically extended portions wherein the malleable metal alloy support is firmly attached to the fabric of the sewing ring.

Each vertically extended portion having mounted adjacent thereto, extended posts having an inside surface, an outside surface, and a distal end. Each extended post has a vertical slit therein through the inner and outer surfaces, and the vertical slits in each inner surface and each outer surface of the extended posts are aligned within each extended post.

Each aligned vertical slit has mounted therein a drivable tab. The drivable tab has a grooved perimeter edge, and each drivable tab has a configuration that matches the apex of the vertically extended portion. Each extended drivable tab post has at least two openings near the distal end.

The valve fixation device comprises a circular plate having a threaded center opening through it, a perimeter edge, a top, and a bottom and six openings smaller than the centered opening and being equally spaced around the perimeter edge and near the bottom.

There are three solid arms attached to the valve fixation device, one arm centered over each pair of small openings, and each arm is hingedly attached to the bottom of the circular plate. Each arm has an inside surface an outside surface, a near end and a distal end, there being at least two openings on the inside surface and near the near end, there being at least two openings in the outside surface and near the near end.

The valve fixation device is threadedly attached to the delivery arm the delivery arm having a distal end and a near end. The delivery arm is hollow and has a lowering mechanism and a raising mechanism contained in it actuated by the movement of a central guide rod that itself has its purpose to threadedly attach to the valve fixation device. The trigger mechanisms are controllable by a trigger tab located in a vertical slot in the wall of the hollow delivery arm, near the distal end serving to actuate the central guide rod.

There is a first continuous braided extremely low profile string that attaches to the circular base plate which commences its continuation through a first opening in the bottom peripheral edge of the circular flat plate, then continues along the outside surface of the first arm of the valve fixation device, continuing through an opening on the outside surface of the first arm, continuing through an opening in the inside surface of the first arm, continuing around the groove in the perimeter of the first drivable tab, continuing through the inside of the near end of the first arm to the outside surface of the first arm, continuing through the bottom of the circular plate to a second opening in the bottom of the circular plate immediately adjacent to the origin of the string at the circular base plate.

The second continuous braided extremely low profile string that attaches to the circular base plate one hundred and twenty degrees from the first string attachment, commences its continuation along the outside surface of the second arm of the valve fixation device, continues through an opening on the outside surface of the second arm, and continues through an opening in the inside surface of the second arm, continuing around the groove in the perimeter of the second drivable tab, continuing through the inside of the near end of the second arm to the outside surface of the second arm, continuing through the opening in the bottom of the circular plate immediately adjacent to the origin of the second string at the base of the circular plate.

The third continuous braided extremely low profile string that attaches to the circular base plate one hundred and twenty degrees from the second string attachment, commences its continuation along the outside surface of the third arm of the valve fixation device, and continues through an opening on the outside surface of the third arm, continuing through an opening in the inside surface of the third arm, continuing around the groove in the perimeter of the third drivable tab, continuing through the inside of the near end of the third arm to the outside surface of the third arm, continuing to, and, attaching to the circular base plate immediately adjacent to the origin of the third string.

Each end of the strings are fixed to the circular plate allowing for simplified release of each individual arm of the fixation device by simply cutting one limb of each of the two arm strings.

Another embodiment of this invention is a combination including a valve fixation device for surmounting a heart valve and a valve fixation device delivery arm.

Yet another embodiment is a valve fixation device for surmounting a heart valve.

DETAILED DESCRIPTION OF THE DRAWINGS

It should be understood that the heart valve per se with the leaflets are not shown in the Figures herein as such devices are well within the knowledge of those skilled in the art and the Figures provide more clarity without that inclusion.

Figure 1:
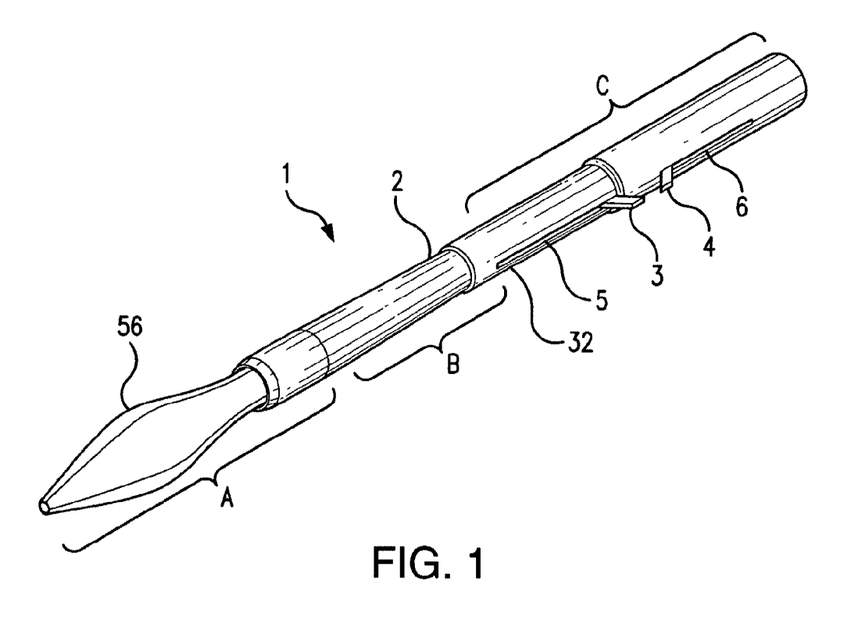
FIG. 1 is a view in perspective of the device of this invention contained within the fully collapsed and housed delivery system.

With reference to FIG. 1, there is shown a transcorporeal delivery system 1 of this invention showing a housing 2, and triggers 3 and 4 for a lowering and raising mechanism, and open slits 5 and 6 in the housing allowing movement of the trigger mechanism 3 and 4.

Figure 2:
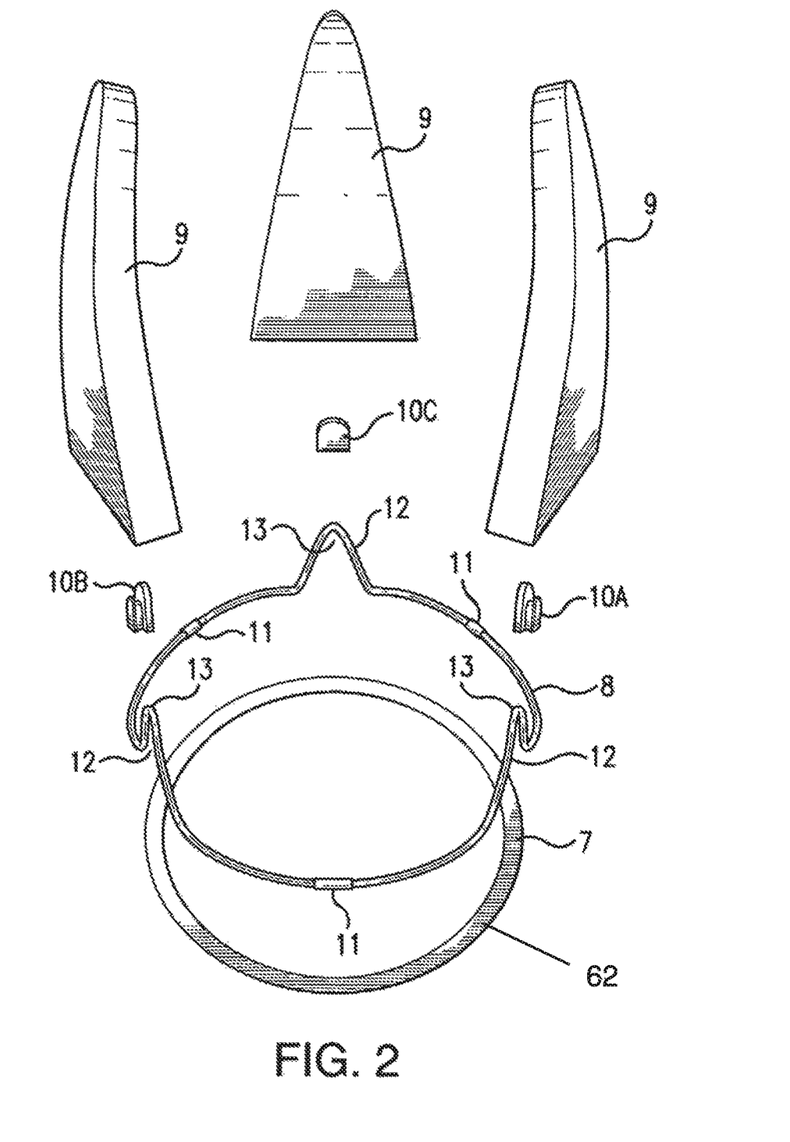
FIG. 2 shows an exploded segment of a valve fixation device along with a sewing ring denoted as within segment A in FIG. 1.

FIG. 2 shows an expanded segment of the valve fixation device 15 (FIG. 3) along with a sewing ring 7. The sewing ring 7 is shown to give perspective to the Figure with regard to how the malleable alloy such as, for example, Nitinol™ malleable metal alloy support 8 and the sewing ring 7 fit with each other. Although not shown, the sewing ring 7 is comprised of thickened flexible material 62 such as Dacron. It is fixed to 15 the base of each post throughout the width of the post. It is compressible between the posts. More specifically, it is compressible between the post and the mid post fixation of the malleable metal alloy wire.

Thus, shown in FIG. 2 are the sewing ring 7, fabric 62, the malleable alloy support 8, three extended posts 9, at least two openings of each vertically extended post, and drivable buttons 10, which will be explained infra. Also note the 20 bands 11, which are located on the malleable alloy support 8 and are spaced equidistantly between the vertical extended portions 12 of the malleable metal alloy support 8. These bands 11 are used to attach the malleable metal alloy support 8 and hence the valve fixation device to the sewing ring 7, using sutures, adhesive, composite materials, or the like, such attachment not being critical as long as the mode allows the attachment to be 25 secure.

Figure 5:
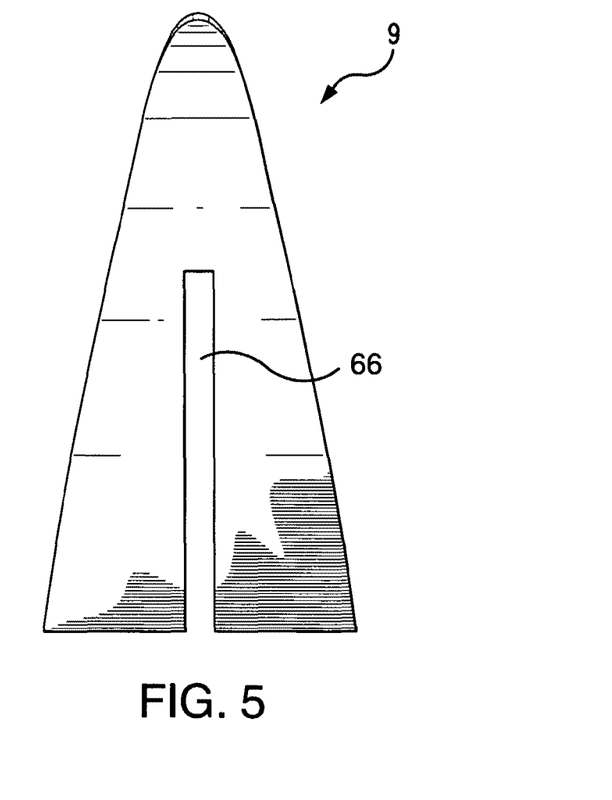
FIG. 5 shows an internal post with exteriors removed showing a vertical slit.

The drive buttons 10A, 10B, and 10C, it will be noted, are configured to fit into the apex 13 of the respective vertical extended portions 12. The drive buttons 10A, 10B, and 10C each have a groove 16 in the perimeter to allow for the placement of a string 14 (not shown in this FIG.), all of which will be described infra. The drive buttons 10A, 10B, and 10C are each driven by manipulation of the string 14 and they ride up and down in a vertical slit 66 in the posts 9 as shown in FIG. 5.

Figure 3:
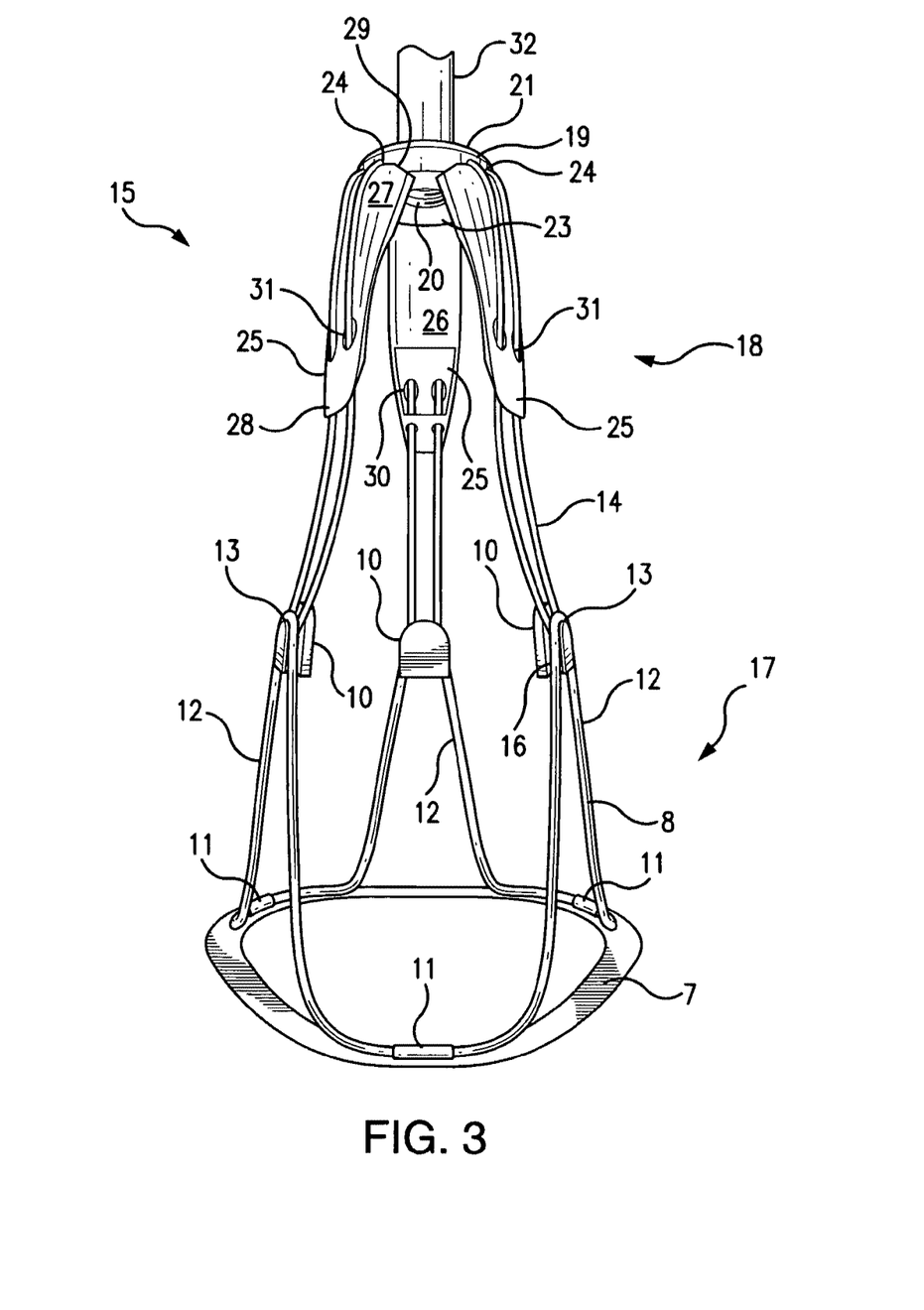
FIG. 3 shows a valve fixation device for an aortic valve with the bottom posts removed (for clarity) with valve fixation device in the expanded mode.

With reference to FIG. 3, there is shown the lower segment 17 and the upper segment 18 of the vertical fixation device 15 in the expanded mode. Shown are the sewing ring 7, the malleable metal alloy ring 8, the fastening bands 11, sutures 53 fastening the malleable metal alloy support 8 at the bands 11, to the sewing ring 7, the vertical extended portions 12, the drivable buttons 10, setting in the apices 13, the peripheral groove 16 (shown only on the right hand side) and the string 14 around the peripheral groove 16. It can be appreciated by those skilled in the art that the remaining two vertical extended components and the accompanying components operate in the same mode as the one described just Supra.

Further with regard to FIG. 3, there is shown the top segment of the upper segment 18 of the vertical fixation device 15 which is composed of a circular plate 19 having a threaded center opening 20. The circular plate 19 has a perimeter edge 21, a top 22 (shown in FIG. 4), a bottom 23, and six openings 35, 39, 40, 45, 46, and 52, smaller than the threaded centered opening 20. The six openings 24 are equally spaced around the circular plate 19.

There are three circular arms 25A, 25B, and 25C, one arm centered over two adjacent small openings 24. The arms 25 and hingedly attached to the bottom 23 of the circular plate 19 and each arm has an inside surface 26, an outside surface 27, a near end 28 and a distal end 29. There is at least two openings 30 on the inside surface 26 near the near end 20 28 and at least two openings 31 in the outside surface 27 and near the near end 28.

The threaded opening 20 in the plate 19 is intended to receive a threaded delivery arm 32 (Segment Con FIG. 1) that is used to collapse and then insert the device through a small opening of the chest cavity or through a thoracoscopic port itself for endothoracic deliver. The threaded delivery arm 32 is solid and permits the lowering 34 and raising mechanism 33 (see FIGS. 617/8 for raising and lowering the components of the device 1. As noted earlier, there are slits S and 6 (FIG. 1) in the wall of the hollow tube to allow the movement of the triggers 3 and 4 and the raising and lowering of the mechanism.

Figure 6:
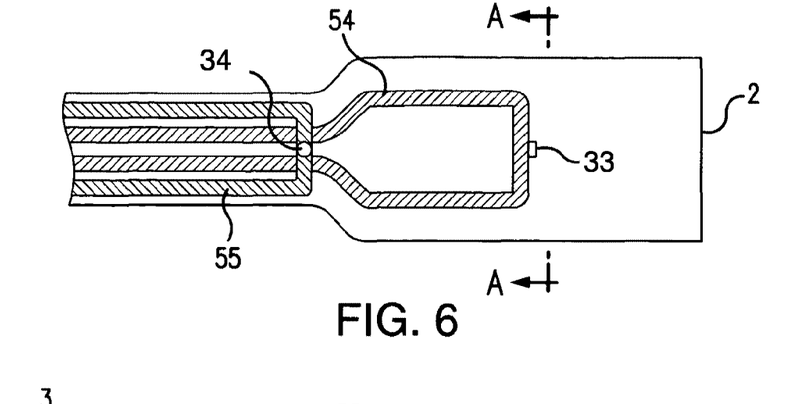
FIG. 6 is a portion of the stem showing in phantom an internal mechanism for manipulating the delivery cocoon 56 and for raising and lowering the valve arms.

FIG. 6 is a portion of the stem showing in phantom an internal mechanism 54 for manipulating the delivery cocoon 56 (FIG. 1) and an internal mechanism 55 for raising and lowering the valve arms.

The mechanism 54 for manipulating the delivery cocoon 56 is comprised of a light weight molded metallic alloy or polymer cradle that resides inside the housing 2 and is held in the center of the internal mechanism 55 (Note FIG. 6), Button 63 is attached to an arm 58 (FIG. 7) so that the cradle can be manipulated by the surgeon.

Figure 7:
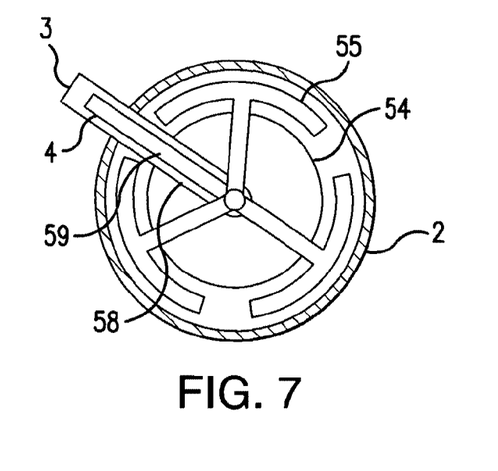
FIG. 7 is a cross sectional view taken through line A-A of FIG. 6.
Figure 8:
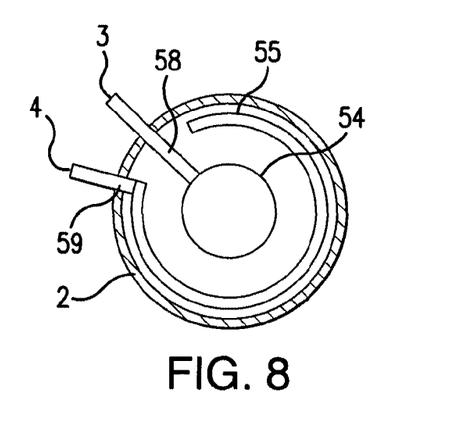
FIG. 8 is a cross sectional view through line B-B of FIG. 9 showing an alternate configuration for an internal mechanism for manipulating the delivery cocoon 56 and for raising and lowering the valve arms.
Figure 9:
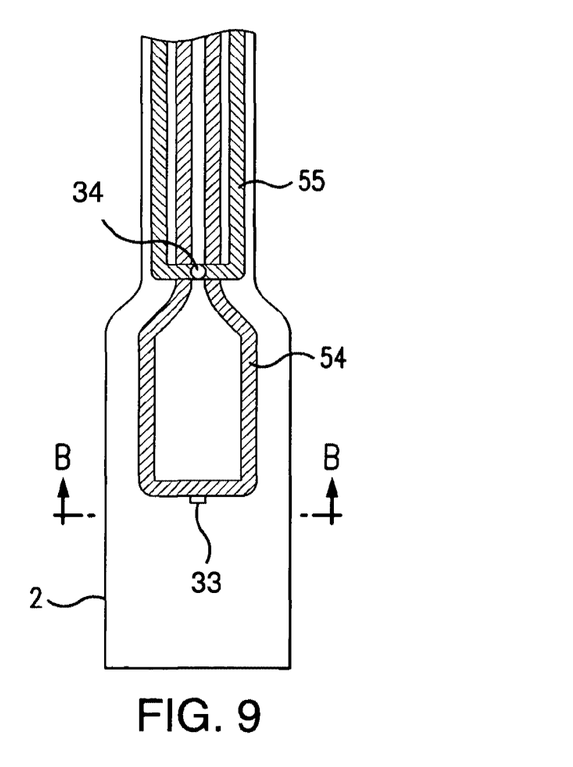
FIG. 9 is a portion of the stem showing in phantom an internal mechanism for manipulating the delivery cocoon 56 and for raising and lowering the valve arms.

The mechanism 55 is for raising and lowering the valve fixation device and is comprised of a lightweight molded metallic alloy or polymer cradle that resides around the outside of the mechanism 54 such that the two mechanisms do not interfere with each other. This mechanism comprises a button 64 that is attached to a handle 59 (FIG. 7).

Figure 4:
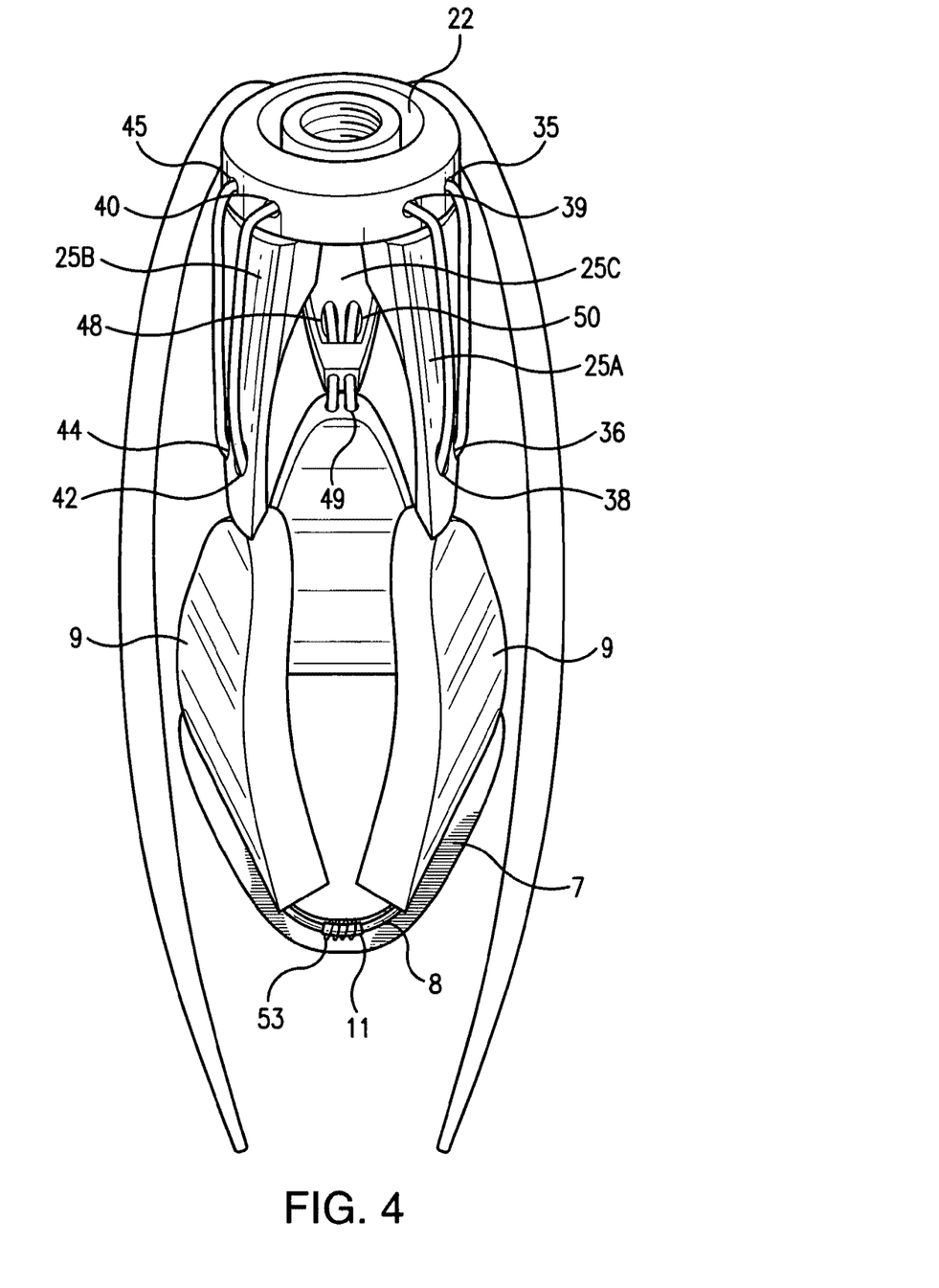
FIG. 4 shows the valve fixation device in an expanded mode.

Referring to FIG. 4, there is a first continuous string 14A that attaches to the circular base plate 19. The string 14 continues through a first opening 35 (FIG. 4) in the bottom 23 of the peripheral edge 21 of the circular plate 19. The string 14 continues along the outside surface 27 of the first arm 25A (FIG. 4) and continues through an opening 36 in the outside surface 27 of the first arm 25A continuing around the groove 16 in the perimeter of the first drivable tab 10A continuing through an opening 37 (not shown) on the inside of the near end of the first ma 25A to the outside surface 27 of the first arm 25A through opening 38 where it enters the bottom 23 of the circular plate 19 through a second opening 39 and is attached to the circular plate 19 near the origin of the first string 14A.

There is a second continuous string 14B that attaches to the circular plate 19 and continues to an opening 40 on the bottom 23 of the circular plate 19 to the outside surface of the second arm 25B.

The second string 14B then continues to an opening 42 in the outside surface of the second arm 25B and continues around the move 16 in the perimeter of the second drivable tab 10B continuing through an opening 43 (not shown) on the inside of the near end of the second arm 25B through an opening 44 to the outside surface of the second era 25B where it enters the bottom 23 of the circular plate 19 and attaches to the circular base plate 19 near the origin of the second string 14B There is a third string 14C that attaches to the circular base plate 19 and then continues to an opening 47 (not shown) in the outside surface of the third arm 25C and continues through opening 48 and continues around the groove 16 in the perimeter of the third drivable tab 10C continuing through an opening 49 to an opening 50 on the inside of the third arm 25C to the outside surface 27 of the third arm 25C to an opening 51 in the outside surface 27 of the third arm 25 C and then into an bottom opening 52 in the plate 19 and then through the delivery arm 32 to connect to the circular base plate 19 near the origin of the third string 14C.

In short, the triggers in the hollow shaft actuate the guide rod that is attached to the circular flat plate 19 exactly akin to an umbrella mechanism with shaft connection to the circular plate 19. The string is attached to the circular base plate 19 and is contiguous from this position carrying a loop down the post arms to the apex of the post, down to the drive tab and up the post, back up the shaft drive arm and fixed to the circular base plate. Note that when the bioprosthesis is rinsed by the surgical assistant in cold saline which is the surgical routine for all bioprostheses, the cold temperature will assist in augmenting the temperature sensitive malleable nature of the malleable metal alloy wire to collapse and facilitate the contraction of the device for sheath deployment and transcorporeal delivery. When the valve is redeployed in the chest cavity and the stitches are cut and the delivery arm is removed, the valve is released.

By this means, the sewing ring 7, the malleable metal alloy support 8 and the heart valve can be manipulated, that is, the sewing ring 7, the malleable metal alloy support 8 and the heart valve, and the accompanying components can be compressed or expanded.

In order to facilitate uniform transcorporeal delivery without other body cavity or chest wall tissues interfering, it is recommended that there be a housing sleeve or delivery cocoon approximately the diameter of the valve with additional length as required. This sleeve will isolate the support ring and valve uniformly in the diameter to also limit kink potential as it enters the body.

It is possible to mount the entire compressed valve assembly within a housing for insertion into the target location. When released from the housing, the sewing ring will expand with a relatively uniform force and rate to apply the target pressure on the vessel wall. The temperature sensitive nature of the malleable metallic alloy, in this case Nitinol, permits re-expansion with warm saline irrigation or once within the chest cavity and approaching body temperature. The housing can then be removed.

Figure 10:
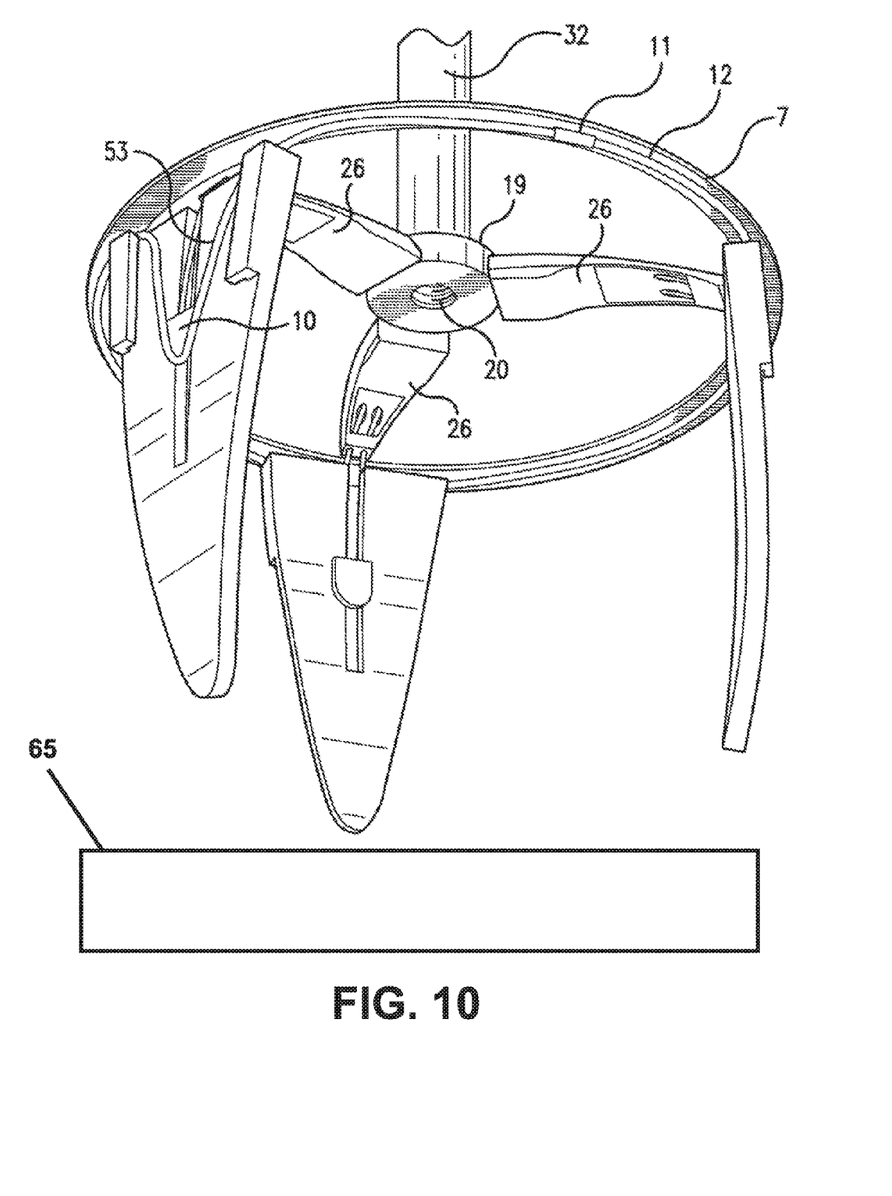
FIG. 10 shows a valve fixation device in an open position showing a mitral valve fixation device.
Figure 11:
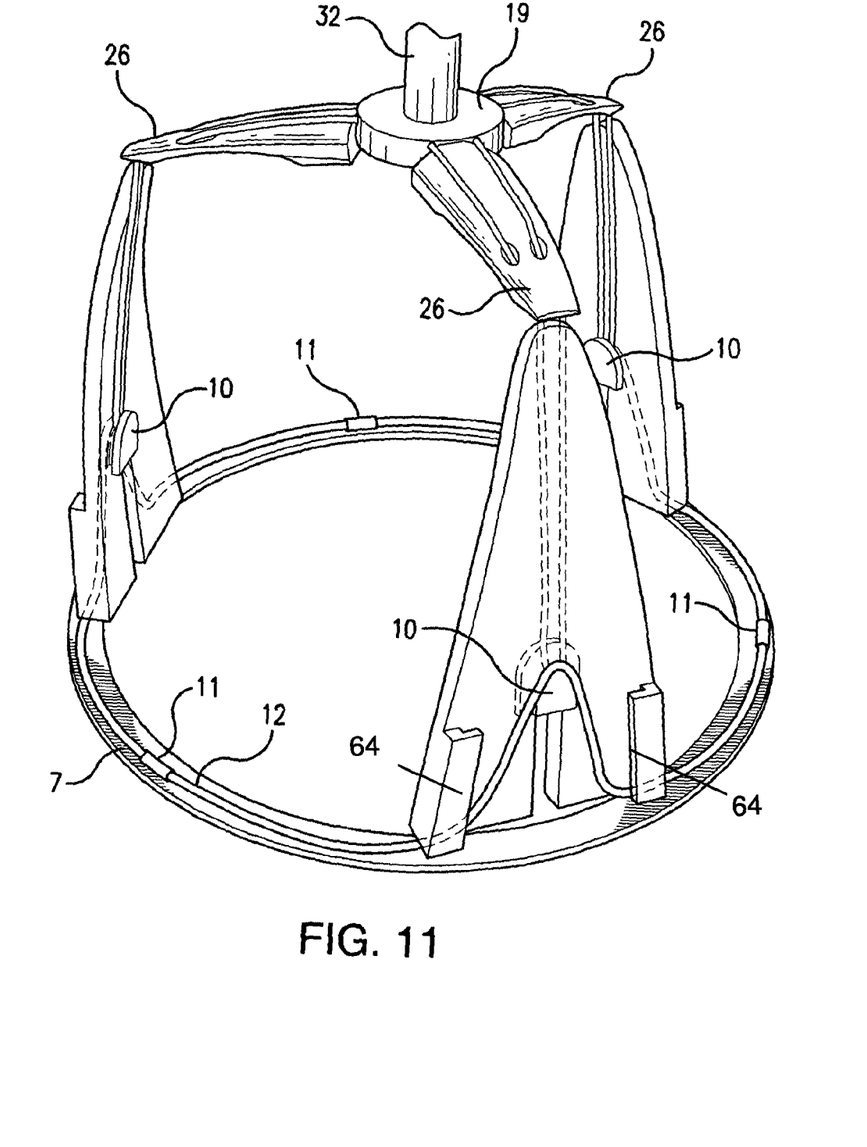
FIG. 11 shows a valve fixation device in an open position showing an aortic valve fixation device.

FIG. 10 shows a valve fixation device in an open position showing a mitral valve replacement valve. FIG. 11 shows a valve fixation device in an open position showing an aortic valve replacement valve.

Figure 12:
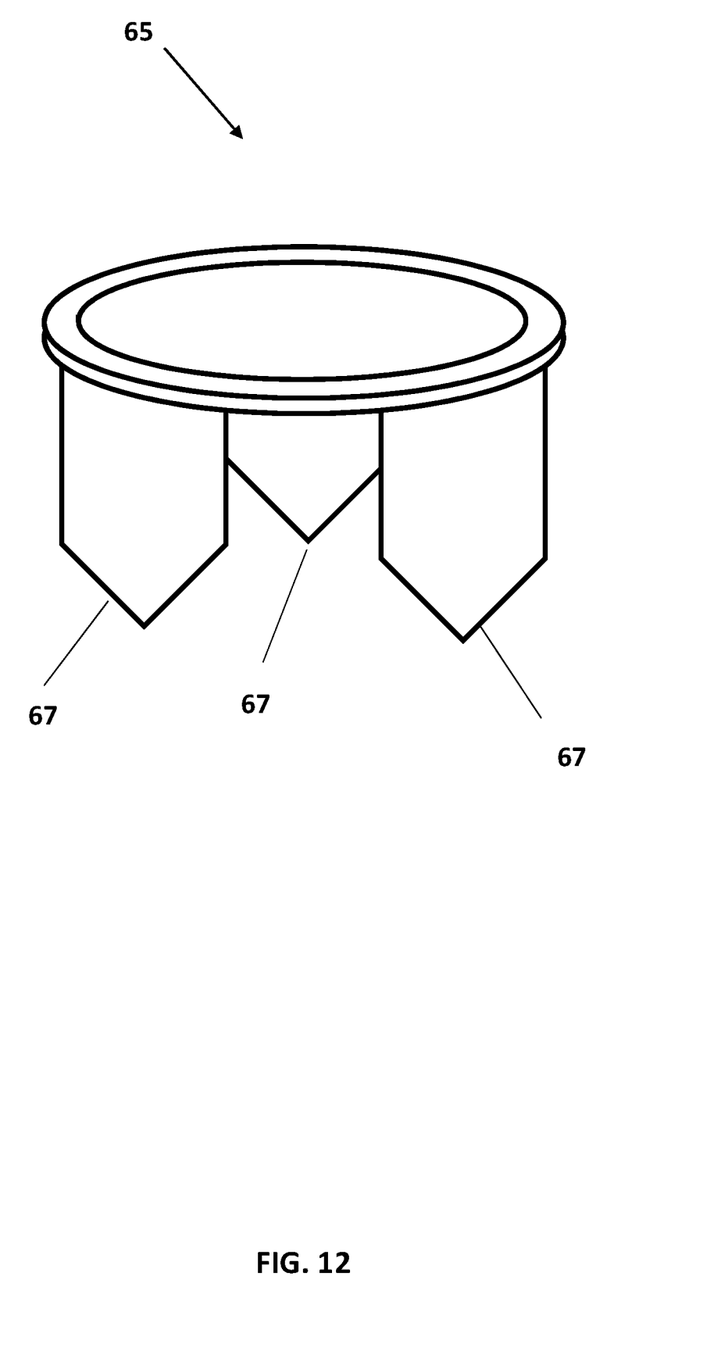
FIG. 12 shows a (prosthetic) heart valve 65 and leaflets 67.

The arrangement of components is structured so that the sewing ring and malleable metal alloy support are near the circular base plate 19 rather than on the bottom of the device as is shown for the aortic valve arrangement found in FIGS. 2 and 11. The numbers of the components in FIGS. 10 and 11 are commensurate with FIG. 2 wherein like components have like numbers. FIG. 10, depicts a box for the presence of a (prosthetic) heart valve 65. In FIG. 11, there are at least two openings of each vertically extended post near the distal end of the vertically extended post 64. FIG. 12 depicts a (prosthetic) heart valve 65 and leaflets 67.

Close working relationship between vendor and composite manufacturer is required to ensure adequate specification of the material for construction with assembly supervision of the formed stented tissue prosthesis without disturbance or alteration is the preparation and attachment of the biologic tissue to the flexible textile material.

The overriding principle for the minimally invasive valve prosthesis is to minimize deviation from current surgical implantation techniques but increase utility for smaller incisions through re-engineering the valve housing and delivery mechanism.

Designed as a modification of leaflet-based valves but not limited to current porcine/bovine stented biologic tissue prostheses, this compression valve design permits for smooth transcorporeal delivery, intracorporeal redeployment, and intracorporeal suturing.

Current bovine/porcine stented valves are tissue-preserved and attached to a flexible textile material covered stent of molded polypropylene and sewing ring. The rigid nature of the plastic housing limits compressibility for transcorporeal delivery. Stentless valves are devoid of housing and are readily deformable but have no means of intracorporeal stabilization for suturing. A valve that can be compressible for transcorporeal delivery via a non rib-spreading incision or 12mm port then redeployed and stabilized for intrathoracic suturing would serve a critical need in minimally invasive valve surgery.

The current compression design does not alter current FDA approved tissue fixation or valve-flexible textile material attachment methods to the prosthesis. Moreover, since the actual compression of the valve tissue is for mere moments, the tissue deformation time remains very limited and less severe compared to the deformation and prolonged crimping of stent-based transcatheter valve prostheses that require percutaneous deployment. The following characteristics encompass the key elements of the valve design. Instead of a covered complete plastic molded stent, the housing includes three posts of molded polypropylene plastic supported by a flexible textile material covered Nitinol™ frame.

The malleable alloy or in the case herein, the Nitinol™ frame is set and pre-molded to the current standard existing bioprosthesis shape (manufacturer specific) and stored at room temperature in its normal open position. A lower profile sewing ring of reinforced flexible textile material is contiguous with the covering.

The posts house a sealed sliding mechanism that is attached to a compression device that is fixed. The internal circumference suture is attached to the post apices for inter-post compression. An external circumference suture is secured to the internal sliding mechanism in each post which is attached to the malleable metal alloy wire to aid in temperature assisted radial base-compression.

The posts are attached to the valve and stored with the prosthesis at room temperature. The valve is then placed in iced saline during the washing protocols for the bioprosthesis. This co-existent cooling process then permits the unique property of malleable metal alloy to be compressed in a controlled manner, The holding/delivery arm is then attached to the circular base, which is attached to the posts on to which the valve is mounted in a simple clockwise manner. Triggering the compression mechanism is then actuated by the surgeon, or surgical scrub assistant, which allows for both inter-post compression and radial base compression of the prostheses.

The compressed prosthesies is then placed in a "Delivery Cocoon" (housing) which protects the device from soft tissue contamination. This delivery cocoon is deployed by a trigger mechanism in a vertical slot on the delivery arm. It is then delivered into the thoracic cavity via a small working incision, a non rib-spreading incision or a 12mm thoracoscopic working port.

While still connected to the delivery system and valve holder, the cocoon is retracted by opposing action on the delivery arm vertical slot trigger used for its deployment. The compression trigger is then released while warm saline or the patient's ambient body temperature actively re-expands the frame to the original open position. This malleable metal alloy enforced base original shape is now maintained due to the warmer body temperature.

The inter-post delivery arms are still attached, thereby allowing the surgeon the stability of suture placement and knot-tying to the native valve annulus. Once the valve is secured in place the three delivery arm sutures are cut and the valve is fully deployed and the delivery arm removed.

The construction will determine optimum wall pressure desired for the expanded product. This is the holding pressure required for the support ring to exert on the vessel walls. Designate this value H (measured in Pascals or pounds per square inch or equivalent).

The construction will determine the desired surface area for contact. This is the approximate cylindrical surface available for support contact. Designate this value SA (measured in square meters or square inches or equivalent). For example, in a 17 mm diameter valve, with a 1 mm contact depth around the perimeter the surface area can be calculated as circumference times depth=SA=(pi*d)*depth=3.14*17 mm*1 mm=53 square millimeters.

One multiplies the holding pressure H by the surface area SA to achieve the expanded force F of the support ring against blood vessel wall. One should ensure that the dimensional analysis yields consistent units of measure. See below for useful conversion factors.

Consider the compressed structure. The malleable metal alloy support ring when received will be cooled slightly to allow easier stress-recovery upon insertion. The system is then crushed mechanically to the appropriate size at the optimum cooling temperature where deformation can take place. This would be limited by valve systems present in order to remain protective as opposed to mechanical integrity properties.

The compression ratio is related to the pressure applied. Depending on the valvular material utilized (biologic tissue or metallic, the ideal value should be confined between maximum compression available for the valve system, and the minimum compression to allow easy insertion during implantation. This would likely be approximately compressed to a diameter of 10 mm undergoing a force of approximately 0.5 Newtons (to be specified by valve manufacturer as required for compression, in conjunction with design based on tissue system forces). The compression ratio will then be (17−10)/17=41%.

What is claimed is:

1. A transcorporeal delivery system comprising:
(A) a prosthetic heart valve and a frame;
(B) a valve fixation device containing said prosthetic heart valve;
(C) a fastening means for attaching a malleable alloy support to said prosthetic heart valve;
(D) a valve fixation device guide rod, and
(E) a mechanism for deploying said prosthetic heart valve, said frame, and valve fixation device, wherein said valve fixation device containing said prosthetic heart valve, said fastening means for attaching a malleable alloy support to said prosthetic heart valve, and, said valve fixation device guide rod, are contained in (F) a housing, and, (G) wherein said prosthetic heart valve and said frame are contained in a delivery cocoon;

said prosthetic heart valve comprising at least two moveable leaflets attached to a fabric covered sewing ring, said sewing ring configured in a shape of a base of said prosthetic heart valve, said sewing ring surmounted by said malleable alloy support, said malleable alloy support being in wire form and having a base configuration essentially corresponding to a configuration of said base of said prosthetic heart valve, wherein said malleable alloy support has three vertically extended portions that are equally spaced from each other around a base; said malleable alloy support having three bands around said base of said malleable alloy support spaced equally between said vertically extended portions;

said malleable alloy support being attached to a fabric of said sewing ring;

three vertically extended posts having mounted adjacent thereto, each said vertically extended posts having an inside surface, an outside surface, and a distal end;

each said extended post having a vertical slit therein through said inner and outer surfaces, said vertical slits in each said inner surface and each said outer surface of said extended posts being aligned within each said extended post;

each said aligned vertical slit having mounted therein a drivable tab, constituting a first drivable tab, a second drivable tab, and a third drivable tab, each said drivable tab having a grooved perimeter edge, each said drivable tab having a configuration that matches an apex of each said vertically extended portion;

each said extended post having at least two openings near said distal end;

said valve fixation device comprising:

(i) a circular plate having a threaded center opening therethrough, a perimeter edge, a top, and a bottom and six openings smaller than said threaded center opening and being equally spaced around said perimeter edge and near said bottom, there being (ii) three solid arms, one said arm centered over two adjacent small openings, said arms being hingedly attached to said bottom of said circular plate, each said arm having an inside surface, an outside surface, a near end and a distal end, there being at least two openings on said inside surface of each said arm and near said near end, there being at least two openings in said outside surface of each said arm and near said near end, said valve fixation device threaddedly attached to a delivery arm, (iii) said delivery arm having a distal end and a near end;

said housing containing a lowering mechanism and a raising mechanism therein, said lowering and raising mechanisms being controllable by trigger tabs located in a vertical slot in a wall of a solid guide rod and near said distal end of said delivery arm, there being a (iv) first continuous braided extremely low profile string that attaches to said circular plate and originates through a first opening in said perimeter edge of said circular plate, then continues along an outside surface of a first arm of said valve fixation device, continuing through an opening on said outside surface of said first arm, continuing through an opening in said inside surface of said first arm, continuing around a groove in a perimeter of said first drivable tab, continuing through an inside surface of a near end of said first arm to said outside surface of said first arm, continuing through said bottom of said circular plate to a second opening in said bottom of said circular plate immediately adjacent to an origin of said first continuous braided extremely low profile string at said circular plate;

(v) a second continuous braided extremely low profile string that attaches to said circular plate one hundred and twenty degrees from a first string attachment, the second continuous braided extremely low profile string originates along an outside surface of a second arm of said valve fixation device, continues through an opening on said outside surface of said second arm, and continues through an opening in an inside surface of said second arm, continuing around a groove in a perimeter of said second drivable tab, continuing through an inside surface of a near end of said second arm to said outside surface of said second arm, continuing through an opening in said bottom of said circular plate immediately adjacent to an origin of said second continuous braided extremely low profile string near said bottom of said circular plate;

(vi) a third continuous braided extremely low profile string that attaches to said circular plate one hundred and twenty degrees from a second string attachment, the third continuous braided extremely low profile string originates along an outside surface of a third arm of said valve fixation device, and continues through an opening on said outside surface of said third arm, continuing through an opening in said inside surface of said third arm, continuing around a groove in a perimeter of said third drivable tab, continuing through an inside surface of a near end of said third arm to said outside surface of said third arm, continuing to, and, attaching to said circular plate immediately adjacent to an origin of said third continuous braided extremely low profile string.

2. A transcorporeal delivery system comprising:

(A) a prosthetic heart valve and a frame;

(B) a valve fixation device containing said prosthetic heart valve;

(C) a fastening means for attaching a malleable alloy support to said prosthetic heart valve;

(D) a valve fixation device guide rod, and (E) a mechanism for deploying said prosthetic heart valve, said frame, and said valve fixation device, wherein said valve fixation device containing said prosthetic heart valve, said fastening means for attaching a malleable alloy support to said prosthetic heart valve, and said valve fixation device guide rod are contained in (F) a housing, and, (G) wherein said prosthetic heart valve and said frame are contained in a delivery cocoon;

said prosthetic heart valve comprising at least two moveable leaflets attached to a fabric covered sewing ring, said sewing ring configured in a shape of a base of said prosthetic heart valve, said sewing ring supporting said malleable alloy support, said malleable alloy support being in wire form and having a base configuration corresponding to a configuration of said prosthetic heart valve base, wherein said malleable alloy support has three vertically extended portions that are equally spaced from each other around a base;

said malleable alloy support having three bands around said base of said malleable alloy support spaced equally between said vertically extended portions;

said malleable alloy support being attached to a fabric of said sewing ring by sutures around said bands;

three vertically extended posts having mounted adjacent thereto, each said vertically extended posts having an inside surface, an outside surface, and a distal end;

each said extended post has a vertical slit therein through said inside and said outside surfaces, said vertical slits in each said inner surface and each said outer surface of said extended posts being aligned within each said extended post;

each said aligned vertical slit having mounted therein a drivable tab, said drivable tab having a grooved perimeter edge, each said drivable tab having a configuration that matches an apex of each said vertically extended portion;

each said extended post having at least two openings near said distal end;

said valve fixation device comprising:
(i) a circular plate having a threaded center opening therethrough, a perimeter edge, a top, a bottom, and six openings smaller than said center opening and being equally spaced around said perimeter edge and near said bottom, there being
(ii) three solid arms, one said arm centered over two adjacent small openings, said arms being hingedly attached to said bottom of said circular plate, each said arm having an inside surface; an outside surface, a near end and a distal end, there being at least two openings on said inside surface of each said arm and near said near end, there being at least two openings in said outside surface of each said arm and near said near end, said valve fixation device threadedly attached to a delivery arm,
(iii) said delivery arm having a distal end and a near end; said housing containing a lowering mechanism and a raising mechanism therein, said lowering and raising mechanisms being controllable by trigger tabs located in a vertical slot in a wall of a solid guide rod and near said delivery arm distal end, there being
(iv) a first continuous braided extremely low profile string that attaches to said circular plate and originates through a small opening in said perimeter edge of said circular plate, continues along an outside surface of a first arm of said valve fixation device, continuing through a first opening on said outside surface of said first arm, continuing through a second opening in said inside surface of said first arm, continuing around a grooved perimeter edge of a first drivable tab, continuing through a third opening to an inside surface of a near end of said first arm to a fourth opening to said outside surface of said first arm, continuing through said bottom of said circular plate to a second small opening in said bottom of said circular plate immediately adjacent to a beginning of said first continuous braided extremely low profile string at said circular plate;
(v) a second continuous braided extremely low profile string that near said bottom of said string attaches to said circular plate one hundred and twenty degrees from a first continuous braided extremely low profile string attachment, the second continuous braided extremely low profile string begins along said outside surface of a second arm of said valve fixation device, continues through a first opening on an outside surface of said second arm, and continues through a second opening in an inside surface of said second arm, continuing around a grooved perimeter edge of a second drivable tab, continuing through a third opening to an inside surface of a near end of said second arm to a fourth opening to said outside surface of said second arm, continuing through an opening in said bottom of said circular plate immediately adjacent to an origin of said continuous braided extremely low profile second string at said circular plate, and
(vi) a third continuous braided extremely low profile string that attaches to said circular plate one hundred and twenty degrees from a second string attachment, the third continuous braided extremely low profile string originates along an outside surface of a third arm of said valve fixation device, and continues through a first opening on said outside surface of said third arm, continuing through a second opening in an inside surface of said third arm, continuing around a grooved perimeter edge of said third drivable tab, continuing through a third opening to an inside surface of a near end of said third arm to a fourth opening to said outside surface of said third arm, continuing to, and, attaching to said circular plate immediately adjacent to a beginning of said third continuous braided extremely low profile string.

3. A valve fixation device for surmounting a prosthetic heart valve, said valve fixation device comprising:
(i) a circular plate having a threaded center opening therethrough, a perimeter edge, a top, and a bottom and six openings smaller than said center opening and being equally spaced around said perimeter edge and near said bottom, there being
(ii) three solid arms, each said arm centered over two adjacent small openings, each said arm being hingedly attached to said bottom of said circular plate, each said arm having an inside surface, an outside surface, a near end and a distal end, there being at least two openings on said inside surface and near said near end, there being at least two openings in said outside surface and near said near end, said valve fixation device threadedly attached a delivery arm,
(iii) said delivery arm having a distal end and a near end;
(iv) a housing, containing a lowering mechanism and a raising mechanism therein, said lowering and said raising mechanisms being controllable by triggers located in a vertical slot in a wall of a solid guide rod and near said delivery arm distal end, there being
(v) a first continuous braided extremely low profile string that attaches to said circular plate and continues through a first small opening in said perimeter edge of said circular plate, then continues along an outside surface of a first arm of said valve fixation device, continuing through a first opening on an outside surface of said first arm, continuing through a second opening in an inside surface of said first arm, continuing around a grooved perimeter edge of a first drivable tab, continuing through a third opening to an inside surface of a near end of said first arm to a fourth opening to an outside surface of said first arm, continuing through said bottom of said circular plate to a second opening in said bottom of said circular plate immediately adjacent to a beginning of said first string at said circular plate;
(vi) a second continuous braided extremely low profile string that attaches to said circular plate one hundred and twenty degrees from a first string attachment, the second continuous braided extremely low profile string continues along said outside surface of a second arm of said valve fixation device, continues through a first opening on said outside surface of said second arm and continues through a second opening in said inside surface of said second arm, continuing around a grooved perimeter edge of a second drivable tab, continuing through a third opening to said inside surface of said near end of said second arm to a fourth opening to said outside surface of said second arm, continuing through an opening in said bottom of said circular plate immediately adjacent to a beginning of said second string at said bottom of said circular plate, and, (vii) a third continuous braided extremely low profile string that attaches to said circular plate one hundred and twenty degrees from a second string attachment, the third continuous braided extremely low profile string continues along said outside surface of a third arm of said valve fixation device, and continues through a first opening on said outside surface of said third arm, continuing through a second opening in an inside surface of said third arm, continuing around a grooved perimeter edge of a third drivable tab, continuing through a third opening to an inside surface of a near end of said third arm to a fourth opening to said outside surface of said third arm, continuing to, and, attaching to said circular plate immediately adjacent to an origin of said third string.

* * * * *